(12) United States Patent
Barrett et al.

(10) Patent No.: US 8,207,344 B2
(45) Date of Patent: Jun. 26, 2012

(54) GPR119 AGONISTS

(75) Inventors: David Gene Barrett, Zionsville, IN (US); Ana Belen Bueno Melendo, Madrid (ES); Jeffry Bernard Franciskovich, Zionsville, IN (US); Bin Liu, Fishers, IN (US); Kumiko Takeuchi, Indianapolis, IN (US)

(73) Assignee: Eli Lilly and Company, Indianpolis, IN (US)

( * ) Notice: Subject to any disclaimer, the term of this patent is extended or adjusted under 35 U.S.C. 154(b) by 169 days.

(21) Appl. No.: 12/834,054

(22) Filed: Jul. 12, 2010

(65) Prior Publication Data

US 2011/0015199 A1    Jan. 20, 2011

Related U.S. Application Data

(60) Provisional application No. 61/245,445, filed on Sep. 24, 2009.

(30) Foreign Application Priority Data

Jul. 15, 2009  (EP) ..................... 09382114

(51) Int. Cl.
C07D 401/00 (2006.01)
C07D 211/08 (2006.01)
A61K 31/445 (2006.01)

(52) U.S. Cl. .................... 546/187; 546/191; 514/316

(58) Field of Classification Search .............. None
See application file for complete search history.

(56) References Cited

FOREIGN PATENT DOCUMENTS

| WO | 2008/025798 | 3/2008 |
|----|-------------|--------|
| WO | 2009/038974 | 3/2009 |

*Primary Examiner* — Janet Andres
*Assistant Examiner* — Heidi Reese
(74) *Attorney, Agent, or Firm* — James B. Myers

(57) ABSTRACT

GPR119 agonist compounds of the formula:

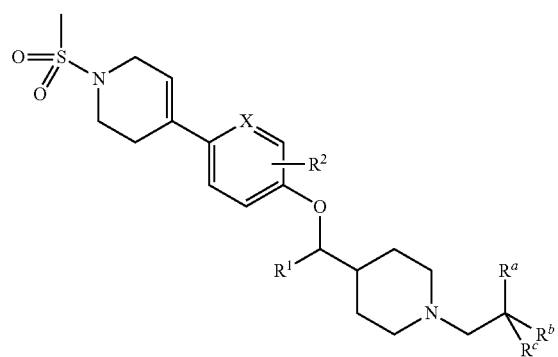

and pharmaceutical compositions for the treatment of diabetes and obesity.

16 Claims, No Drawings

GPR119 AGONISTS

This application claims the benefit of U.S. Provisional Application Ser. No. 61/245,445, filed Sep. 24, 2009 and EP 09382114.8, filed Jul. 15, 2009, which are hereby incorporated by reference.

GPR119 is a G-protein-coupled receptor largely confined in humans to pancreatic (β-cells) and intestinal tissues (enteroendocrine cells) and has been studied and described using various synonyms including SNORF25, RUP3, GPCR2, 19AJ, OSGPR116 and glucose-dependent insulinotropic receptor.

The pharmacology and therapeutic potential for GPR119 has been reviewed recently (Br. J. Pharmacol. 2008, 153, S76-S81), disclosing GPR119 as an interesting target for the treatment of diabetes and obesity.

A number of synthetic agonists of GPR119 have been disclosed for the treatment of diabetes and obesity, for example those disclosed in WO 09/038974. There remains a need for alternative GPR119 agonists as antidiabetic and antiobesity therapies.

Oral administration is typically the preferred route of administration for antidiabetic and antiobesity therapies. For compounds to display good oral bioavailability, they typically must have sufficient aqueous solubility to allow absorption, and sufficient metabolic stability to minimize first pass degradation in the liver.

The compounds of Formula I have been found to be agonists of GPR119 in vitro. Certain compounds of the present invention have been shown to stimulate GIP secretion in vivo. Certain compounds of the present invention exhibit greater potency than existing agonists. Certain compounds of the present invention have good oral bioavailability.

The present invention is directed to compounds of Formula I which are agonists of the G-protein-coupled receptor GPR119, pharmaceutical compositions containing them as active ingredient, and to their use in the treatment or prevention of diabetes or obesity, in particular Type II diabetes.

The present invention provides a compound of the formula:

The present invention provides a pharmaceutical composition comprising a compound of Formula I, or a pharmaceutically acceptable salt thereof, and a pharmaceutically acceptable diluent or carrier.

The present invention provides a compound of Formula I, or a pharmaceutically acceptable salt thereof, for use in therapy. The present invention also provides a compound of Formula I, or a pharmaceutically acceptable salt thereof for use in the treatment of diabetes and obesity. The present invention further provides a compound of Formula I, or a pharmaceutically acceptable salt thereof for use in the treatment of diabetes or obesity. In another aspect of the present invention, there is provided the use of a compound of Formula I, or a pharmaceutically acceptable salt thereof, for the manufacture of a medicament for the treatment of diabetes and obesity. The present invention further provides the use of a compound of Formula I, or a pharmaceutically acceptable salt thereof, for the manufacture of a medicament for the treatment of diabetes or obesity The present invention also provides a method for the treatment of diabetes and obesity, which comprises administering an effective amount of a compound of Formula I, or a pharmaceutically acceptable salt thereof, to a human being or animal in need thereof. The present invention further provides a method for the treatment of diabetes or obesity, which comprises administering an effective amount of a compound of Formula I, or a pharmaceutically acceptable salt thereof, to a human being or animal in need thereof. It is preferred that the compounds of the present invention be used in the treatment of diabetes or obesity, in particular type II diabetes.

A preferred species of the compounds of Formula I are compounds of the formula:

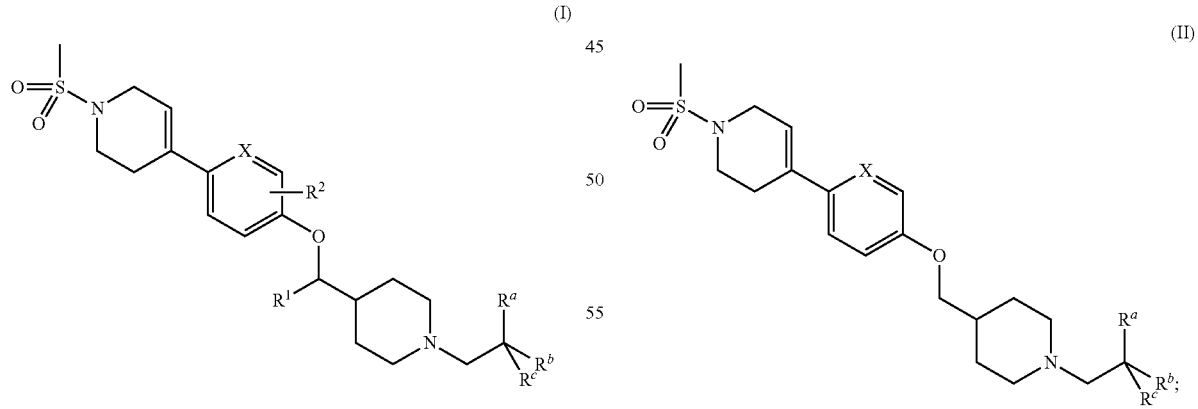

wherein;
X is selected from N and CH;
$R^a$ is selected from F and $CF_3$;
$R^b$ and $R^c$ are independently selected from F and methyl or combine to form a $C_{3-5}$ cycloalkyl ring;
$R^1$ is selected from H and methyl;
$R^2$ is selected from H and F;
or a pharmaceutically acceptable salt thereof.

or a pharmaceutically acceptable salt thereof, wherein X, $R^a$, $R^b$, and $R^c$ are as defined herein.

A preferred species of the compounds of Formula I are compounds of the formula:

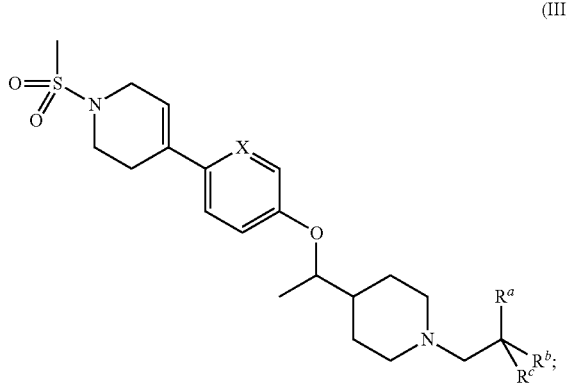

(III)

or a pharmaceutically acceptable salt thereof, wherein X, $R^a$, $R^b$, and $R^c$ are as defined herein.

Certain classes of compounds of Formula I, II or III are preferred. The following enumerated selections describe such preferred classes:
1) X is N;
2) X is CH;
3) $R^2$ is H;
4) $R^a$ is F;
5) $R^a$ is $CF_3$;
6) $R^b$ and $R^c$ are independently selected from F and methyl or combine to form $C_3$ cycloalkyl;
7) $R^b$ and $R^c$ are methyl or combine to form $C_3$ cycloalkyl;
8) X is N and $R^b$ and $R^c$ are methyl or combine to form $C_3$ cycloalkyl;
9) X is CH and $R^b$ and $R^c$ are methyl or combine to form $C_3$ cycloalkyl;
10) $R^b$ and $R^c$ are methyl and $R^a$ is F;
11) $R^b$ and $R^c$ combine to form $C_3$ cycloalkyl and $R^a$ is $CF_3$.

Pharmaceutically acceptable salts of each of the compounds of the present invention are contemplated within the scope of the present application.

Preferred compounds of the present invention include 5-[1-(2-Fluoro-2-methyl-propyl)-piperidin-4-ylmethoxy]-1'-methanesulfonyl-1',2',3',6'-tetrahydro-[2,4']bipyridinyl; and 1-Methanesulfonyl-4-{4-[1-(1-trifluoromethyl-cyclopropyl-methyl)-piperidin-4-ylmethoxy]-phenyl}-1,2,3,6-tetrahydro-pyridine.

As used throughout this specification, it is to be understood that where a group is qualified by "defined herein" or "herein defined" that said group encompasses the first occurring and broadest definition as well as each and all of the particular definitions of that group.

As used above and throughout the description of the invention, the following terms, unless otherwise indicated, will have the following meaning:

As used herein the term "$C_3$-$C_5$ cycloalkyl" is taken to mean cyclopropyl, cyclobutyl and cyclopentyl. Preferred $C_3$-$C_5$ cycloalkyl groups include cyclopropyl and cyclobutyl; another preferred group is cyclopropyl.

As used herein the terms "isomer 1" and "isomer 2" relate to the specific enantiomers of final compounds or intermediates, "isomer 1" relating to the first compound to elute from the described chromatographic process and "isomer 2" the second. Where the term "isomer 1" or "isomer 2" is first attributed to an intermediate, the term is retained through to the final compound.

As used herein the term "pharmaceutically acceptable salts" refers to salts of the compounds of the present invention which are substantially non-toxic to living organisms. Such salts and common methodology for preparing them are well known in the art. See, e.g., P. Stahl, et al., Handbook of Pharmaceutical Salts: Properties Selection and Use, (VCHA/Wiley-VCH, 2002); and J. Pharm. Sci. 66, 2-19 (1977). Preferred pharmaceutically acceptable salts include hydrochloride, mesylate and fumerate; more preferred salts are hydrochloride and mesylate.

The compounds of the present invention are preferably formulated as pharmaceutical compositions administered by a variety of routes. Most preferably, such compositions are for oral administration. Such pharmaceutical compositions and processes for preparing same are well known in the art. See, e.g., Remington: The Science and Practice of Pharmacy (A, Gennaro, et al., eds., 19th ed., Mack Publishing Co., 1995). Preferred pharmaceutical compositions include a compound of the present invention admixed with vehicle selected from the group consisting of 0.5 M phosphoric acid (100 mg/ml maximum concentration); hydroxyethylcellolose (1% w/v), polysorbate 80 (0.25% v/v), antifoam (0.05% v/v) and deionised water (110 mg/ml maximum concentration); and vitamin E TPGS (d-alpha-tocopheryl polyethylene glycol 1000 succinate) (10% v/v), antifoam (0.05% v/v) and deionised water (250 mg/ml maximum concentration).

In a further aspect of the invention the present compounds are administered in combination with one or more therapeutic ingredients. Such therapeutic ingredients include for example metformin or a DPPIV inhibitor e.g. sitagliptin.

Administration in combination includes simultaneous, separate or sequential administration.

For administration in combination for the treatment of diabetes it is preferred that the compounds of the present invention are simultaneously, separately or sequentially administered with metformin. For administration in combination for the treatment of obesity it is preferred that the compounds of the present invention are simultaneously, separately or sequentially administered with sitagliptin.

The following Schemes, Preparations and Examples are provided to better elucidate the practice of the present invention. Suitable reaction conditions for the steps of these Schemes, Preparations and Examples are well known in the art and appropriate modification of reaction conditions, including substitution of solvents and co-reagents are within the ability of the skilled artisan. Temperatures indicated in the following Preparations and Examples correspond to external bath temperature, unless otherwise indicated.

Furthermore, the skilled artisan will appreciate that in some circumstances, the order in which moieties are introduced is not critical. The particular order of steps required to produce the compounds of Formula I is dependent upon the particular compound being synthesized, the starting compound, and the relative lability of the substituted moieties, as is well appreciated by the skilled chemist. The skilled artisan will appreciate that not all substituents are compatible with all reaction conditions. These compounds may be protected or modified at a convenient point in the synthesis by methods well known in the art.

Suitable protecting groups include those described in T. W. Greene, "Protective Groups in Organic Synthesis", John Wiley and Sons, New York, N.Y., 1991, hereafter referred to as "Greene". Greene indicates appropriate conditions for "protection" and "de-protection" of suitable protecting groups to be used by the skilled artisan.

The intermediates and final products of the present invention may be further purified, if desired by common techniques such as recrystallization or chromatography over solid supports such as silica gel or alumina.

The compound names for the Examples of the present invention are generated using AutoNom 2000.

Abbreviations used herein are defined as follows:

"h" means hours; "min" means minutes; "cAMP" means Cyclic Adenosine Monophosphate; "DMEM" means Dulbecco's Modified Eagle's Medium; "HTRF" means Homogenous Time-Resolved Fluorescence; "PBS" means Phosphate Buffered Saline; "IBMX" means Isobutylmethylxanthine; "BSA" means Bovine Serum Albumin; "FBS" means Fetal Bovine Serum; "EBSS" means Earle's Balanced Salt Solution; "EDTA" means Ethylene Diamine Tetraacetic Acid; "NADPH" means Nicotinamide Adenosine Dinucleotide Phosphate; "HEC" means Hydroxyethyl Cellulose; LC-ESI/MS" means Liquid Chromatography-Electrospray Ionization Mass Spectrometry; "Pg" means Protecting Group; "Tf" means trifluoromethyl sulfonyl; "Ts" means para-toluene sulfonyl; and "Ms" means methyl sulfonyl.

compound (b). Compound (b) is reacted with an aldehyde under standard reductive amination conditions, with a suitable reducing agent such as sodium triacetoxyborohydride in a suitable solvent such as dichloromethane to provide the final compound (I). Alternatively compound (b) is reacted with an appropriately substituted acid using a coupling reagent such as o-benzotriazol-1-yl-N,N,N',N'-tetramethyluronium tetrafluoroborate and a suitable base such as diisopropylethylamine in a suitable solvent such as dimethylformamide at elevated temperature. The isolated product is reacted with a suitable reducing agent such as lithium aluminum hydride in a suitable solvent such as tetrahydrofuran at elevated temperature to provide the final compound (I). Alternatively compound (b) is reacted with R'OY and a suitable base such as potassium carbonate in a suitable solvent such as acetonitrile at elevated temperature to provide the final compound (I).

Alternatively, where $R^a$ is F and both $R^b$ and $R^c$ are methyl the compounds I' may be prepared as described below in Scheme B.

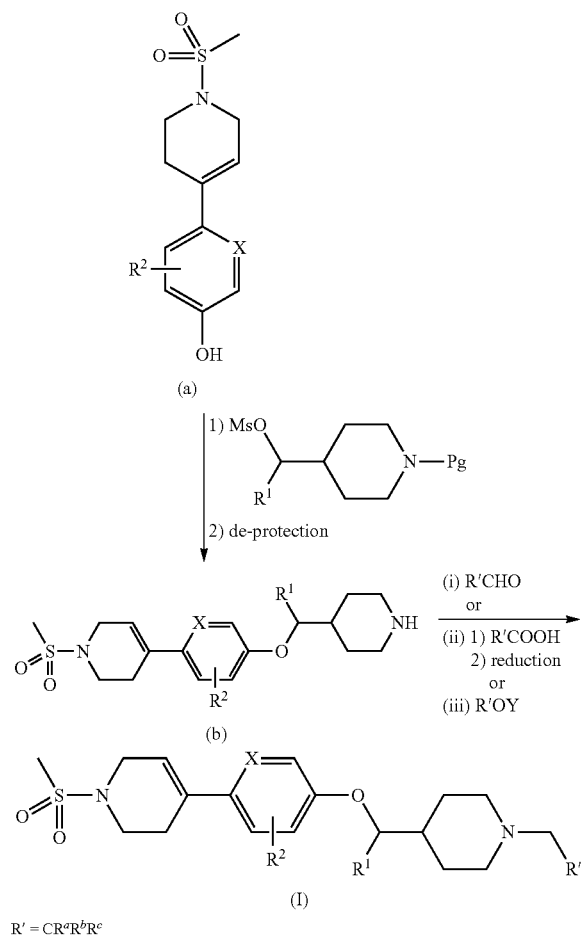

Scheme A (a)

1) MsO— ...R¹... N—Pg
2) de-protection (b)

(i) R'CHO
or
(ii) 1) R'COOH
2) reduction
or
(iii) R'OY (I)

R' = CR$^a$R$^b$R$^c$
Y = Tf, Ts or Ms

The starting hydroxyl (a) is reacted with a mesylate bearing a piperidine with an appropriate protecting group such as carboxylic acid tert-butyl ester and a suitable base such as potassium carbonate in a suitable solvent such as acetonitrile at elevated temperature. The isolated product is de-protected under conditions well known to the skilled artisan to provide

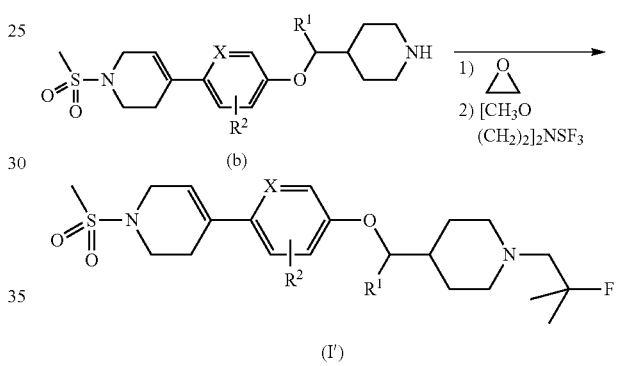

Scheme B (b)

1) <epoxide>
2) [CH$_3$O(CH$_2$)$_2$]$_2$NSF$_3$ (I')

The starting piperidine (b) is reacted with 2,2-dimethyloxirane under an inert atmosphere such as nitrogen in a suitable solvent such as methanol. The isolated product is reacted with a suitable fluorinating agent such as bis(2-methoxyethyl)aminosulfur trifluoride in a suitable solvent such as dichloromethane to provide the final compound (I').

The requisite hydroxyl (a) may be prepared as described below in Scheme C.

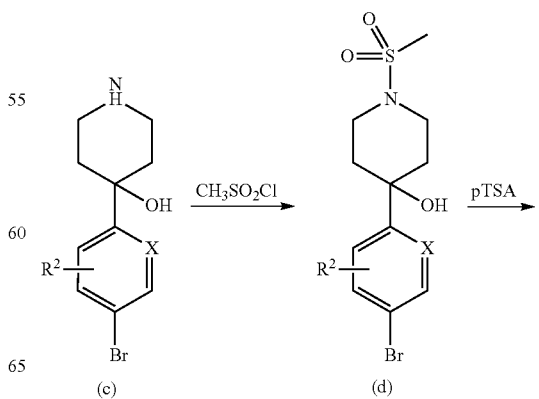

Scheme C (c) → CH$_3$SO$_2$Cl → (d) → pTSA →

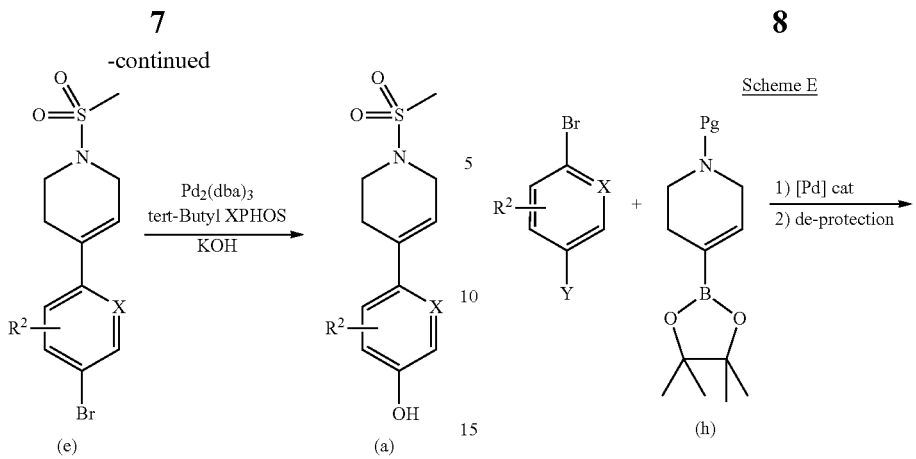

The starting piperidin-4-ol (c) is reacted with methanesulfonyl chloride and a suitable base such as triethylamine or pyridine in a suitable solvent such as dichloromethane or tetrahydrofuran to provide compound (d). Compound (d) is reacted with p-toluenesulfonic acid in a suitable solvent such as toluene at elevated temperature to provide the tetrahydropyridine (e). Compound (e) is reacted by the method described in J. Am. Chem. Soc 2006, 128, 10694-10695 using potassium hydroxide, 2-di-tert-butylphosphino-2',4',6'-tri-i-propyl-1,1'-biphenyl and tris(dibenzylideneacetone)dipalladium in a suitable solvent such as dioxane/water at elevated temperature to provide the tetrahydro-pyridine compound (a).

Alternatively, the requisite bromo (e) and hydroxyl (a) may be prepared as described in Schemes D and E.

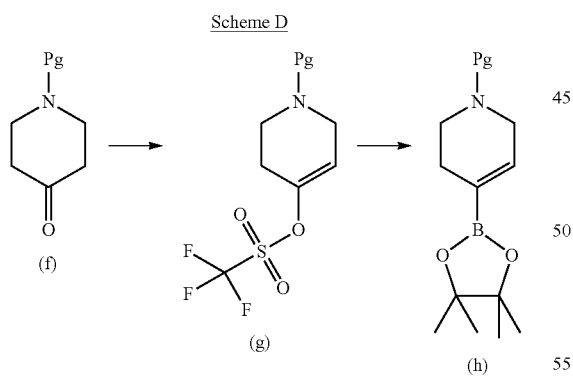

The starting piperidone (f) is mixed with a suitable base such as lithium diisopropylamide in a suitable solvent such as tetrahydrofuran at reduced temperature and reacted with N-phenylbis(trifluoromethanesulfonimide) to provide the compound (g). The tetrahydro-pyridine compound (g) is reacted with bis(pinacolato)diboron, (1,1'-bis(diphenylphosphino)ferrocene)palladium(II) chloride, 1,1'-bis(diphenylphosphino)ferrocene, and potassium acetate in a suitable solvent such as 1,4-dioxane at elevated temperature to provide the compound (h).

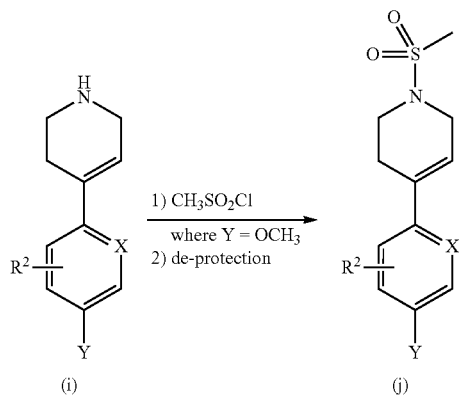

Y = $OCH_3$, and Br
Z = OH and Br

The starting bromide is reacted with a boronate compound (h) bearing an appropriate protecting group such as carboxylic acid tert-butyl ester, a suitable palladium catalyst such as tetrakis(triphenylphosphine)palladium and a suitable base such as cesium carbonate in a suitable solvent such as dioxane/water at elevated temperature. The isolated product is de-protected under conditions well known to the skilled artisan to provide compound (i). Compound (i) is reacted with methanesulfonyl chloride and a suitable base such as triethylamine in a suitable solvent such as dichloromethane to provide the compound (j). Where the substituent Y is $OCH_3$ an additional deprotection step, using conditions well known to the skilled artisan, is required to provide compound (j).

Alternatively, compounds where $R^1$ is H may be prepared as described below in Scheme F.

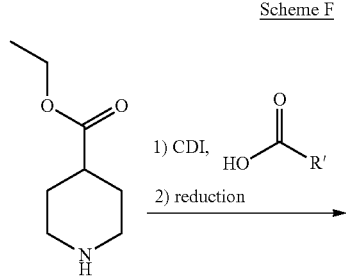

-continued

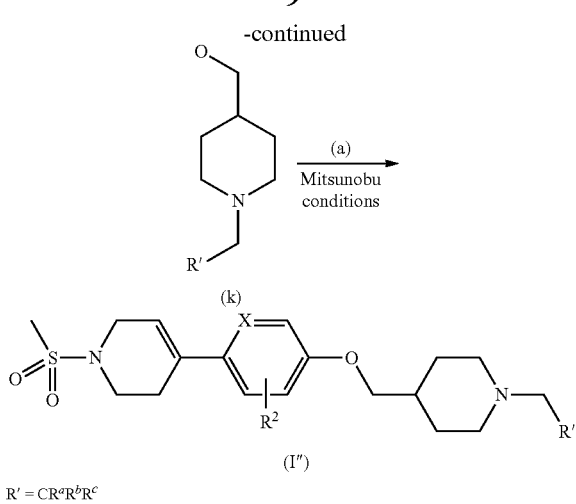

R' = CR$^a$R$^b$R$^c$

An appropriately substituted acid is reacted with 1,1'-Carbonyldiimidazole in a suitable solvent such as tetrahydrofuran, to which is added piperidine-4-carboxylic acid ethyl ester. The isolated product is reacted with a suitable reducing agent such as lithium aluminium hydride in a suitable solvent such as tetrahydrofuran to provide the compound (k). The compound (k) is reacted with compound (a) using standard Mitsunobu conditions such as diisopropyl azodicarboxylate and triphenylphosphine, at reduced temperature, in a suitable solvent such as tetrahydrofuran to provide the final compound (I'').

Preparation 1

4-(1-Methanesulfonyl-1,2,3,6-tetrahydro-pyridin-4-yl)-phenol

1: 4-(4-Bromo-phenyl)-1-methanesulfonyl-piperidin-4-ol

Methanesulfonyl chloride (21.91 g, 14.81 mL, 191.30 mmol) is added slowly (10 min) to a solution of 4-(4-bromophenyl)-4-piperidinol (50.00 g, 191.30 mmol) and triethylamine (29.04 g, 40.00 mL, 286.95 mmol) in tetrahydrofuran (575 mL) at 23° C. (internal temperature) under nitrogen atmosphere. The mixture is stirred at 23° C. for 30 min. 500 mL of 1 M aq hydrochloric acid are added and the mixture is stirred for 10 min. The mixture is extracted with ethyl acetate (2×500 mL) the organic layers are combined, dried over anhydrous sodium sulfate, filtered and the solvent is removed to obtain 60.0 g of the title compound as a white solid. MS m/e ($^{79}$Br/$^{81}$Br) 333, 335 (M+1).

2: 4-(4-Bromo-phenyl)-1-methanesulfonyl-1,2,3,6-tetrahydro-pyridine

A mixture of 4-(4-bromo-phenyl)-1-methanesulfonyl-piperidin-4-ol (60.00 g, 179.51 mmol) and p-toluenesulfonic acid (9.37 g, 53.85 mmol) in toluene (1.08 L) is stirred at 100° C. for 16 h. The reaction is cooled to 23° C. and successively washed with 2 M aq. sodium hydroxide to pH 10, and water. The phases are separated and the organic layer is dried over anhydrous sodium sulfate, filtered and the solvent is removed. Methyl tert-butyl ether (200 mL) is added and the solid is filtered and washed with methyl tert-butyl ether to obtain 35.0 g of the title compound as a pale brown solid. MS m/e ($^{79}$Br/$^{81}$Br) 315, 317 (M+1).

3: 4-(1-Methanesulfonyl-1,2,3,6-tetrahydro-pyridin-4-yl)-phenol

A mixture of 4-(4-bromo-phenyl)-1-methanesulfonyl-1,2,3,6-tetrahydro-pyridine (23.50 g, 74.32 mmol), potassium hydroxide (14.72 g, 222.95 mmol), 2-di-tert-butylphosphino-2',4',6'-tri-i-propyl-1,1'-biphenyl (2.52 g, 5.95 mmol) and tris(dibenzylideneacetone)dipalladium (0) (1.36 g, 1.49 mmol) is purged with nitrogen, and then deoxygenated 1,4-dioxane (150 mL) and deoxygenated water (150 mL) are added. The mixture is stirred at 100° C. for 1 h. The mixture is cooled to 23° C. and 1 M aq hydrochloric acid is added until pH 2-3. The aqueous layer is extracted with ethyl acetate. The organic layers are combined, dried over anhydrous sodium sulfate, filtered, and the solvent is removed to obtain a red solid. Diethyl ether is added and the solid is filtered to obtain 16 g of the title compound as an off-white solid. MS (m/z) 254 (M+1).

Preparation 2

1-Methanesulfonyl-4-[4-(piperidin-4-ylmethoxy)-phenyl]-1,2,3,6-tetrahydro-pyridine 1: 4-Methanesulfonyloxymethyl-piperidine-1-carboxylic acid tert-butyl ester Methanesulfonyl chloride (29.26 g, 19.77 mL, 255.47 mmol) is added slowly (10 min) under nitrogen atmosphere to a solution of tert-butyl 4-(hydroxymethyl)piperidine-1-carboxylate (50.00 g, 232.24 mmol) and triethylamine (35.25 g, 48.56 mL, 348.36 mmol) in anhydrous dichloromethane (700 mL) at 9° C. (internal temperature). The mixture is stirred at 23° C. for 16 h. The reaction mixture is successively washed with 1 M aq hydrochloric acid, water, and brine. The organic layer is dried over anhydrous sodium sulfate, filtered, and the solvent is removed to obtain 60 g of the title compound as a white solid. MS (m/z) 316 (M+23).

2: 4-[4-(1-Methanesulfonyl-1,2,3,6-tetrahydro-pyridin-4-yl)-phenoxymethyl]-piperidine-1-carboxylic acid tert-butyl ester A mixture of 4-methanesulfonyloxymethyl-piperidine-1-carboxylic acid tert-butyl ester (17.95 g, 61.19 mmol), Preparation 1 (15.50 g, 61.19 mmol) and potassium carbonate (16.91 g, 122.37 mmol) in acetonitrile (120 mL) is heated under reflux for 18 h. The reaction is cooled to 23° C. and the solvent is removed. The residue is dissolved with a mixture of 1 L of dichloromethane and 500 mL of water and phases are separated. The organic layer is washed with brine, dried over sodium sulfate, filtered and evaporated. The solid obtained is treated with 250 mL of methyl tert-butyl ether to afford 22.0 g of the title product. MS (m/z) 473 (M+23).

3: 1-Methanesulfonyl-4-[4-(piperidin-4-ylmethoxy)-phenyl]-1,2,3,6-tetrahydro-pyridine Trifluoroacetic acid (2.98 g, 1.97 mL, 26.10 mmol) is added to a solution of 4-[4-(1-methanesulfonyl-1,2,3,6-tetrahydro-pyridin-4-yl)-phenoxymethyl]-piperidine-1-carboxylic acid tert-butyl ester (1.20 g, 2.61 mmol) in dichloromethane (13 mL). The mixture is stirred at 23° C. for 30 min. 2 M aq. sodium hydroxide is added. The resulting white precipitate is filtered and washed with water. The mother liquor is extracted with dichloromethane. The combined organic layers are dried over anhydrous sodium sulfate, filtered, and the solvent is removed to obtain a white solid which is combined with the initial precipitate and dried under high vacuum for 16 h. Diethyl ether is added and the solid is filtered and washed with ethyl acetate to obtain 0.810 g of an off-white solid. MS (m/z) 351 (M+1).

Preparation 3

4-(4,4,5,5-Tetramethyl-[1,3,2]dioxaborolan-2-yl)-3, 6-dihydro-2H-pyridine-1-carboxylic acid tert-butyl ester 1: 4-Trifluoromethanesulfonyloxy-3,6-dihydro-2H-pyridine-1-carboxylic acid tert-butyl ester In a 3 necked flask with addition funnel, temperature probe and magnetic stirrer, a solution of diisopropylamine (32.30 g, 44.93 mL, 319.20 mmol) in tetrahydrofuran (160 mL) is cooled to −10° C. (internal temperature). n-Butyl lithium (133.0 mL, 332.50 mmol, 2.5 M in hexanes,) is added dropwise (10 min, temperature change from −10° C. to 1° C.). The mixture is stirred at −10° C. for 10 min, and then cooled to −60° C. (internal temperature, −75° C. bath). A solution of N-tert-butoxycarbonyl-4-piperidone (53.00 g, 266.00 mmol) in tetrahydrofuran (160 mL) is added dropwise (10 min). The mixture is stirred at −60° C. for 1.5 h, a solution of N-phenylbis(trifluoromethanesulphonimide) (99.78 g, 279.30 mmol) in tetrahydrofuran (160 mL) is added dropwise at −60° C. (5 min). More tetrahydrofuran (40 mL) is added and the mixture is allowed to warm to 23° C. for 16 h. Saturated aq sodium bicarbonate (400 mL) is added to the mixture, which is then extracted with ethyl acetate (3×400 mL). Combined organic layers are washed with brine, dried over anhydrous magnesium sulfate, filtered and concentrated. The resulting mixture is passed through a silica gel plug, eluting with hexane:ethyl acetate 4:1 to give 78.00 g of the title compound as a yellow oil. The material is used in the next step without further purification. $^1$H NMR (CDCl$_3$) δ (ppm): 1.47 (s, 9H), 2.43-2.47 (m, 2H), 3.63 (t, 2H), 4.03-4.11 (m, 2H), 5.76 (s, 1H).

2: 4-(4,4,5,5-Tetramethyl-[1,3,2]dioxaborolan-2-yl)-3,6-dihydro-2H-pyridine-1-carboxylic acid tert-butyl ester 4-Trifluoromethanesulfonyloxy-3,6-dihydro-2H-pyridine-1-carboxylic acid tert-butyl ester (235.43 mmol; 78.00 g) is dissolved in 1,4-dioxane (1170 mL) and the solution is degassed for 5 min. Bis(pinacolato)diboron (65.76 g, 258.97 mmol), 1,1'-bis(diphenylphosphino)ferrocene (6.53 g, 11.77 mmol), (1,1'-bis(diphenylphosphino)ferrocene)palladium (II) chloride (9.61 g, 11.77 mmol) and potassium acetate (69.32 g, 706.28 mmol) are added, and the mixture is stirred under nitrogen at 85° C. for 3 h. The mixture is cooled to 23° C. and stirred for 16 h. The mixture is filtered through diatomaceous earth, washed with ethyl acetate, and concentrated in vacuo. The crude product is purified by flash chromatography on silica gel, eluent hexane:ethyl acetate (12:1 to 4:1) to give 72.00 g of the title compound, which is used in the next step without further purification. MS (m/z) 254 (M−55).

Preparation 4

4-(1-Methanesulfonyloxy-ethyl)-piperidine-1-carboxylic acid tert-butyl ester

1: 4-(1-Hydroxy-ethyl)-piperidine-1-carboxylic acid tert-butyl ester

To a solution of N-tert-butoxycarbonyl-4-piperidinecarboxaldehyde (32.20 g, 151.45 mmol) in tetrahydrofuran at −78° C. is added methyl magnesium bromide (2 M in diethyl ether, 100.96 mL, 302.89 mmol). The reaction is stirred at −78° C. for 4.5 h, and then warmed to −50° C. for 30 min. The reaction is quenched with water at −50° C. and allowed to warm to room temperature for 16 h. The solvents are removed and the material is partitioned between diethyl ether and 0.1 M hydrochloric acid. The mixture is extracted with diethyl ether. The combined organic layers are washed with 0.1 M hydrochloric acid, saturated aqueous sodium bicarbonate and brine, dried over magnesium sulfate, filtered, and concentrated to dryness. The crude is purified by flash chromatography over silica gel to afford 16.90 g of the title compound as a colourless oil. MS (m/z) 229 (M+1).

2: 4-(1-Methanesulfonyloxy-ethyl)-piperidine-1-carboxylic acid tert-butyl ester

To a solution of 4-(1-hydroxy-ethyl)-piperidine-1-carboxylic acid tert-butyl ester (18.24 g, 79.54 mmol) in dichloromethane (400 mL) and triethylamine (12.20 mL, 87.49 mmol) at 0° C. is added methanesulfonyl chloride (9.23 mL, 119.30 mmol). The reaction is allowed to warm to room temperature over 16 h. The mixture is washed with 0.1 M hydrochloric acid, saturated aqueous sodium bicarbonate, water, and brine. The material is dried over magnesium sulfate, filtered, and concentrated to dryness. The crude material is purified by flash chromatography over silica gel to afford 22.65 g of the title compound as a colourless oil. $^1$H NMR (CDCl$_3$) δ (ppm): 1.19-1.30 (m, 2H), 1.39 (d, 3H), 1.44 (s, 9H), 1.6-1.8 (m, 3H), 2.66 (m, 2H), 2.99 (s, 3H), 4.16 (m, 2H), 4.62 (t, 1H).

Preparation 5

4-{1-[4-(1-Methanesulfonyl-1,2,3,6-tetrahydro-pyridin-4-yl)-phenoxy]-ethyl}-piperidine 1: 4-{1-[4-(1-Methanesulfonyl-1,2,3,6-tetrahydro-pyridin-4-yl)-phenoxy]-ethyl}-piperidine-1-carboxylic acid tert-butyl ester To a solution of Preparation 1 (2.35 g, 9.27 mmol) and Preparation 4 (2.85 g, 9.27 mmol) in acetonitrile (93.00 mL) is added cesium carbonate (3.02 g, 9.27 mmol) and 18-crown-6 (0.49 g, 1.85 mmol). The mixture is heated to 80° C. for 72 h. The mixture is concentrated in vacuo and the remaining material is partitioned between ethyl acetate and water. The organic layer is washed with 1 M sodium hydroxide and brine. The material is dried over magnesium sulfate, filtered, and concentrated to dryness. The resulting material is diluted with 10 mL of diethyl ether, sonicated for 3 min, and the remaining solid filtered, and dried under vacuum to afford 2.02 g of the title product as a white solid. MS (m/z) 487 (M+32), 365 (M−55).

2: 4-{1-[4-(1-Methanesulfonyl-1,2,3,6-tetrahydro-pyridin-4-yl)-phenoxy]-ethyl}-piperidine To a solution of 4-{1-[4-(1-methanesulfonyl-1,2,3,6-tetrahydro-pyridin-4-yl)-phenoxy]-ethyl}-piperidine-1-carboxylic acid tert-butyl ester (1.16 g, 2.50 mmol) in dichloromethane (25 mL) is added trifluoroacetic acid (1.32 mL, 17.48 mmol). The reaction is stirred at room temperature for 18 h. The mixture is concentrated in vacuo and diluted with 3 mL of ethyl acetate. 2 M aqueous sodium hydroxide is added to produce a white solid. The solid is filtered and dried to afford 0.86 g of the title compound. MS (m/z) 365 (M+1). The title compound (0.320 g, 0.88 mmol) is separated into its enantiomers using an eluent of 0.2% dimethylethylamine in 2:3 acetonitrile:methanol on a 4.6×150 mm Chiralcel AD-H column at 1 mL/min to afford 0.115 g of isomer 1 (100% ee, RT=5.27 min) MS (m/z) 365 (M+1) and 0.112 g of isomer 2 (100% ee, RT=8.59 min). MS (m/z) 365 (M+1).

Preparation 6

4-(1'-Methanesulfonyl-1',2',3',6'-tetrahydro-[2,4']bipyridinyl-5-yloxymethyl)-piperidinium dihydrochloride salt 1: 5-Bromo-3',6'-dihydro-2'H-[2,4']bipyridinyl-1'-carboxylic acid tert-butyl ester A mixture of 2,5-dibromopyridine (50.00 g, 211.07 mmol), Preparation 3 (71.79 g, 232.17 mmol), 2 M aqueous sodium carbonate (158.30 mL, 316.60 mmol) and tetrakis(triphenylphosphine)palladium (0) (7.32 g, 6.33 mmol) in 1,4-dioxane (633 mL) is heated at 100° C. under a nitrogen atmosphere overnight. The reaction is allowed to cool to room temperature, filtered through diatomaceous earth and washed with ethyl acetate. The organic layer is washed with 500 mL of water, dried over magnesium sulfate, filtered and evaporated. The crude material is purified by silica gel chromatography eluting with hexane:ethyl acetate 6:1 to afford 55 g of a white solid. MS m/e ($^{79}$Br/$^{81}$Br) 339, 341 (M+1 of both isotopes).

2: 5-Bromo-1',2',3',6'-tetrahydro-[2,4']bipyridinyl-1'-ium; dihydrochloride salt 4 M Hydrogen chloride (170.24 g, 162.13 mL, 648.52 mmol) in 1,4-dioxane is added to a solution of 5-bromo-3',6'-dihydro-2'H-[2,4']bipyridinyl-1'-carboxylic acid tert-butyl ester (55.00 g, 162.13 mmol) in dichloromethane (810 mL). The mixture is stirred at room temperature for 12 h and heated at 40° C. for 6 h. The mixture is evaporated and the solid is filtered and washed with methyl t-butyl ether. The solid is dried in an oven at 40° C. for 12 h to provide 50 g of the title compound. MS m/e ($^{79}$Br/$^{81}$Br) 238/240 (M+1).

3: 5-Bromo-1'-methanesulfonyl-1',2',3',6'-tetrahydro-[2,4']bipyridinyl

The title compound is prepared essentially by the method of Preparation 1 (step 1) using 5-bromo-1',2',3',6'-tetrahydro-[2,4']bipyridinyl-1'-ium; dihydrochloride salt a starting material. MS m/e ($^{79}$Br/$^{81}$Br) 316/318 (M+1).

4: 1'-Methanesulfonyl-1',2',3',6'-tetrahydro-[2,4']bipyridinyl-5-ol

The title compound is prepared essentially by the method of Preparation 1 (step 3) using 5-bromo-1'-methanesulfonyl-1',2',3',6'-tetrahydro-[2,4']bipyridinyl as starting material. MS (m/z) 255 (M+1).

5: 4-(1'-Methanesulfonyl-1',2',3',6'-tetrahydro-[2,4']bipyridinyl-5-yloxymethyl)-piperidine-1-carboxylic acid tert-butyl ester The title compound is prepared essentially by the method of Preparation 2 (step 2) using 1'-methanesulfonyl-1',2',3',6'-tetrahydro-[2,4']bipyridinyl-5-ol as starting material. MS (m/z) 452 (M+1).

6: 4-(1'-Methanesulfonyl-1',2',3',6'-tetrahydro-[2,4']bipyridinyl-5-yloxymethyl)-piperidinium; dihydrochloride salt The title compound is prepared essentially as in step 2 of this preparation. MS (m/z) 352 (M+1)

EXAMPLE 1

4-{4-[1-(1-Fluoro-cyclopentylmethyl)-piperidin-4-ylmethoxy]-phenyl}-1-methanesulfonyl-1,2,3,6-tetrahydro-pyridine

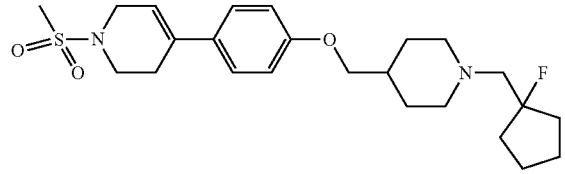

1: 1-Oxa-spiro[2.4]heptane-2-carbonitrile

A 1 M solution of potassium tert-butoxide in tert-butyl alcohol (184.4 mL, 184.4 mmol) is added slowly to a solution of chloroacetonitrile (10.8 mL, 167.6 mmol) and cyclopentanone (15.0 mL, 167.6 mmol) in anhydrous t-butyl alcohol (33 mL). The reaction is stirred at room temperature for 16 h. The mixture is filtered through diatomaceous earth, the solvent is removed, and the residue is diluted with water. The mixture is neutralized with 30% aq.sodium dihydrogen phosphate solution and extracted with diethyl ether. The organic layers are combined, dried over anhydrous sodium sulfate, filtered, and the solvent is removed. The residue is purified by flash chromatography over silica gel to obtain 14.1 g of the title compound as a colourless oil. $^1$H NMR (CDCl$_3$) δ (ppm): 3.46 (s, 1H), 1.65-2.20 (m, 8H).

2: (1-Fluoro-cyclopentyl)-hydroxy-acetonitrile

Anhydrous dichloromethane (3 mL) and a 70% w/w solution of hydrogen fluoride (2.68 mL, 20.44 mmol) in pyridine are mixed in a polyethylene bottle at 0° C. under a nitrogen atmosphere. A solution of 1-oxa-spiro[2.4]heptane-2-carbonitrile (3.30 g, 26.76 mmol) in anhydrous dichloromethane (3.2 mL) is added slowly. The reaction is stirred at 0° C. for 1 h and at room temperature for 1 h. The mixture is cooled at 0° C. and a saturated solution of sodium carbonate is added carefully. The aqueous layer is extracted with diethyl ether. The organic layers are combined, washed with water and brine, dried over anhydrous sodium sulfate, filtered, and the solvent is removed. The residue is purified by chromatography in a 20 g silica gel cartridge eluting with hexane:diethyl ether (100:0 to 80:20) to obtain 1.7 g of desired compound as a colourless oil. $^1$H NMR (CDCl$_3$) δ (ppm): 4.47 (d, 1H), 3.50 (bs, 1H), 2.12-1.67 (m, 8H).

3: 1-Fluoro-cyclopentanecarbaldehyde

A solution 25% of sodium hydroxide (7.00 mL, 72.8 mmol) in water is added to a solution of (1-fluoro-cyclopentyl)-hydroxy-acetonitrile (0.50 g, 3.5 mmol) in ethanol (10 mL) and the reaction is stirred at room temperature for 15 min. The mixture is diluted with water and diethyl ether and the aqueous layer is extracted with diethyl ether. The organic layers are combined, washed with water and brine, dried over anhydrous sodium sulfate, filtered, and the solvent is removed under vacuum to obtain 430 mg of a yellow oil that is used without further purification.

4: 4-{4-[1-(1-Fluoro-cyclopentylmethyl)-piperidin-4-ylmethoxy]-phenyl}-1-methanesulfonyl-1,2,3,6-tetrahydro-pyridine Acetic acid (0.024 mL, 0.42 mmol) and 1-fluoro-cyclopentanecarbaldehyde (0.367 mL, 3.70 mmol) are added to a suspension of Preparation 2 (150 mg, 0.427 mmol) in dichloromethane (4 mL) and the mixture is stirred at 40° C. for 45 min. Sodium triacetoxyborohydride (236.22 mg, 1.07 mmol) is added and the mixture is stirred at 40° C. for 1.5 h. Saturated aqueous solution of sodium bicarbonate is added and the mixture is extracted with ethyl acetate. The organic layers are combined, washed with water and brine, dried over anhydrous sodium sulfate, filtered, and the solvent is removed. The residue is chromatographed on a 10 g silica gel cartridge eluting with dichloromethane:ethyl acetate 20%, 50%, and 100% to obtain a pale yellow solid. The compound is triturated with diethyl ether and filtered to obtain 25 mg of the title compound as a white solid. MS (m/z) 451 (M+1).

EXAMPLE 2

4-{4-[1-(2-Fluoro-2-methyl-propyl)-piperidin-4-ylmethoxy]-phenyl}-1-methanesulfonyl-1,2,3,6-tetrahydro-pyridine

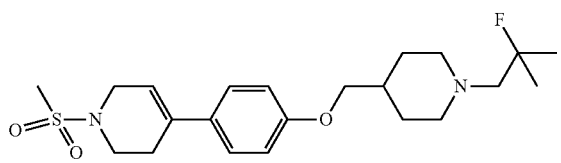

1: 2-Fluoro-1-{4-[4-(1-methanesulfonyl-1,2,3,6-tetrahydro-pyridin-4-yl)-phenoxymethyl]-piperidin-1-yl}-2-methyl-propan-1-one Diisopropylethylamine (1.60 g, 2.16 mL, 12.40 mmol) is added to a suspension of Preparation 2 (1.60 g, 4.13 mmol), o-benzotriazol-1-yl-N,N,N',N'-tetramethyluronium tetrafluoroborate (1.99 g, 6.20 mmol) and 2-fluoro-2-methyl-propionic acid (0.48 g, 0.54 mL, 4.55 mmol) in anhydrous dimethylformamide (20 mL) and the mixture is stirred at 40° C. for 1 h. The reaction mixture is diluted with ethyl acetate and washed successively with 1 M aqueous hydrochloric acid, water, and 2 M aqueous sodium hydroxide. The organic layer is dried over anhydrous sodium sulfate, filtered, and the solvent is removed. The residue is purified by silica gel chromatography on a silica gel cartridge eluting with dichloromethane:ethyl acetate 0%, 5% then 10% to obtain 1.0 g of the title compound as a pale brown solid. MS (m/z) 439 (M+1).

2: 4-{4-[1-(2-Fluoro-2-methyl-propyl)-piperidin-4-ylmethoxy]-phenyl}-1-methanesulfonyl-1,2,3,6-tetrahydro-pyridine To a solution of 2-fluoro-1-{4-[4-(1-methanesulfonyl-1,2,3,6-tetrahydro-pyridin-4-yl)-phenoxymethyl]-piperidin-1-yl}-2-methyl-propan-1-one (1.00 g, 2.28 mmol) in tetrahydrofuran (23 mL) at rt is added via cannula a 1 M solution of lithium aluminum hydride in tetrahydrofuran (7.18 g, 7.98 mL, 7.98 mmol). After 1 h, sodium sulfate decahydrate is added carefully. The mixture is stirred for 15 min and the solid is filtered off and washed with dichloromethane. The solvent is removed and the residue is purified via silica gel chromatography, eluting with dichloromethane:ethyl acetate 5.6:1 to 2:1 to obtain a solid. Diethyl ether is added and the solid is filtered and washed with diethyl ether and ethyl acetate to obtain 0.245 g of the title compound as a white solid. MS (m/z) 425 (M+1).

The following compounds are prepared essentially by the same method as outlined in Example 2.

| Example | Chemical name/structure | MS (m/z) |
|---|---|---|
| 3 | 1'-Methanesulfonyl-5-[1-(3,3,3-trifluoro-2,2-dimethyl-propyl)-piperidin-4-ylmethoxy]-1',2',3',6'-tetrahydro-[2,4']bipyridinyl | 476 (M + 1) |
| 4 | 1-Methanesulfonyl-4-{4-[1-(1-trifluoromethyl-cyclobutylmethyl)-piperidin-4-ylmethoxy]-phenyl}-1,2,3,6-tetrahydro-pyridine | 487 (M + 1) |
| 5 | 1-Methanesulfonyl-4-{4-[1-(1-trifluoromethyl-cyclopentylmethyl)-piperidin-4-ylmethoxy]-phenyl}-1,2,3,6-tetrahydro-pyridine | 501 (M + 1) |

EXAMPLE 6

5-[1-(2-Fluoro-2-methyl-propyl)-piperidin-4-yl-methoxy]-1'-methanesulfonyl-1',2',3',6'-tetrahydro-[2,4']bipyridinyl

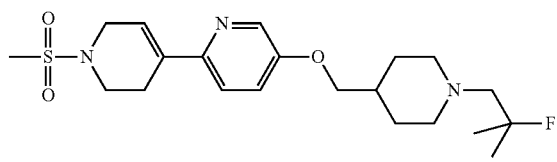

1: 4-(1'-Methanesulfonyl-1',2',3',6'-tetrahydro-[2,4']bipyridinyl-5-yloxymethyl)-piperide Preparation 6 (47 g, 114.5 mmol) is dissolved in 2 M aqueous solution of sodium hydroxide (500 mL) and extracted with diclormethane (2×500 mL). The organic layer is dried over magnesium sulphate, filtered and evaporated to obtain 40 g of the title compound as a light yellow solid. MS (m/z) 352 (M+1).

2: 1-[4-(1'-Methanesulfonyl-1',2',3',6'-tetrahydro-[2,4']bipyridinyl-5-yloxymethyl)-piperidin-1-yl]-2-methyl-propan-2-ol To a solution of 4-(1'-methanesulfonyl-1',2',3',6'-tetrahydro-[2,4']bipyridinyl-5-yloxymethyl)-piperide (40 g, 113.81 mmol) in methanol (230 mL) at 25° C. under nitrogen atmosphere is added 2,2-dimethyloxirane (15.18 mL; 170.71 mmol) in one portion and the reaction is stirred at 25° C. for 16 h. Water (500 mL) is added and the precipitate is filtered, washed with methyl t-butyl ether (250 mL) and dried to obtain 33 g of the title compound as a light yellow solid. MS (m/z) 424 (M+1).

3: 5-[1-(2-Fluoro-2-methyl-propyl)-piperidin-4-yl-methoxy]-1'-methanesulfonyl-1',2',3',6'-tetrahydro-[2,4']bipyridinyl To a solution of 2-methyl-1-[4-[[6-(1-methylsulfonyl-3,6-dihydro-2H-pyridin-4-yl)-3-pyridyl]oxymethyl]-1-piperidyl]propan-2-ol (33 g; 77.91 mmoles) in dichloromethane (155 mL) is added bis(2-methoxyethyl)aminosulfur trifluoride (16.63 mL; 85.70 mmoles) at an internal temperature of 22-23° C. The reaction is stirred at 25° C. for 2 h. Aqueous saturated solution of sodium bicarbonate is added to pH 7. Layers are separated, the aqueous layer is extracted with dichloromethane (2×500 mL), the combined organic layers are dried over magnesium sulphate, filtered and concentrated.

The crude material is purified by silica gel chromatography eluting with 98:2 dichloromethane:methanol. The solid is triturated with 500 mL of methyl t-butyl ether and filtered. The solid is dried in an oven at 40° C. for 3 days to obtain 24 g of the title compound as a white solid. MS (m/z) 426 (M+1).

An alternative method for the preparation of Example 6 is as follows:

1: 4-[4-(1-Methanesulfonyl-1,2,3,6-tetrahydro-pyridin-4-yl)-phenoxymethyl]-piperidine-1-carboxylic acid tert-butyl ester To a 3-necked flask with a mechanical stirrer are added 4-(1-hydroxy-methyl)-piperidine-1-carboxylic acid tert-butyl ester (350 g, 1.63 mol), triethylamine (247 g, 2.44 mol) and dichloromethane (1750 mL). The solution is stirred at 0° C. for 30 min. Methanesulfonyl chloride (223.5 g, 1.95 mol) is added slowly at 0~5° C. The mixture is stirred at ~5° C. for 1.5 h. 1050 mL of 0.5 N solution of aq. hydrochloride are added to the mixture dropwise at 0~15° C. and the resulting solution is stirred for 30 min. Layers are separated and the organic layer is washed with 1050 mL of water and concentrated to dryness. 700 mL of methyl tert-butyl ether are added and the mixture is refluxed for 0.5 h. After the mixture is slowly cooled to ~5° C., the suspension is filtered. The solid is stirred with 500 mL of methyl tert-butyl ether and filtered to dryness to provide 434 g of an off-white solid with 98.6% HPLC purity.

2: 4-(1'-Methanesulfonyl-1',2',3',6'-tetrahydro-[2,4']bipyridinyl-5-yloxymethyl)-piperidine-1-carboxylic acid tert-butyl ester To a 3-necked flask is added 1'-methanesulfonyl-1',2',3',6'-tetrahydro-[2,4']bipyridinyl-5-ol (254.3 g, 1.0 mol) followed by 4-(1-methanesulfonyloxy-ethyl)-piperidine-1-carboxylic acid tert-butyl ester (396.1 g, 1.34 mol) and potassium carbonate (248.8 g, 1.8 mol). Dimethylformamide (3800 mL) is added and the mixture is heated at 80~90° C. for 6 h. 3810 mL of water are added dropwise at 70~80° C. The mixture is cooled slowly to 20~30° C. and filtered. The cake is slurried with 1000 mL of water, concentrated and dried under vacuum to provide 407 g of a solid with 97.13% HPLC purity.

3: 4-(1'-Methanesulfonyl-1',2',3',6'-tetrahydro-[2,4']bipyridinyl-5-yloxymethyl)-piperidine To a 3-necked flask with a mechanical stirrer is added 4-(1'-methanesulfonyl-1',2',3',6'-tetrahydro-[2,4']bipyridinyl-5-yloxymethyl)-piperidine-1-carboxylic acid tert-butyl ester (407 g, 0.90 mol) and 6N aq hydrogen chloride (2000 mL, 12.0 mol) is added dropwise at 25° C. The mixture is stirred mechanically at 25° C. for 0.5 h. 1000 mL of dichloromethane are added at 25° C. and the mixture is stirred for 20~30 min. Layers are separated and aqueous NaOH (1500 mL, 11.6 mol) is added dropwise to the aqueous solution to pH=9~10 at 25° C. 3200 mL of dichloromethane are added and the mixture is stirred at 25~30° C. for 40 min. Aqueous solution of NaOH (300 mL, 2.3 mol) is added dropwise to pH >14, until complete dissolution of the solid, the solution is stirred for 20 to 30 min and layers are separated. The aqueous layer is extracted with 1700 mL of dichloromethane. The combined organic layers are washed with 900 mL of water and concentrated. The residue is used for the next step without further purification.

4: 1-[4-(1'-Methanesulfonyl-1',2',3',6'-tetrahydro-[2,4']bipyridinyl-5-yloxymethyl)-piperidin-1-yl]-2-methyl-propan-2-ol 4-(1'-Methanesulfonyl-1',2',3',6'-tetrahydro-[2,4']bipyridinyl-5-yloxymethyl)-piperidine is suspended in 800 mL of methanol and added to an autoclave with a mechanical stirrer. 1500 mL of methanol are added and then dimethyloxirane (117 g, 1.62 mol) is added. The mixture is stirred at 60~70° C. for 88 h, cooled to 25~30° C. and concentrated to 1000 mL. The mixture is heated at 60~70° C. and 4200 mL of water are added. The resulting mixture is stirred at 60~70° C. during 30 min and cooled slowly to 0~5° C. in 1.5~2 h. It is stirred at this temperature for 30 minutes and filtered. The cake is slurried with $H_2O$: MeOH=3:1 (600 mL) pre-cooled to 0~5° C. and concentrated (2×). The product is dried under vacuum at 40~50° C. to provide 320 g of off-white solid with 98.3% HPLC purity.

5: 5-[1-(2-Fluoro-2-methyl-propyl)-piperidin-4-ylmethoxy]-1'-methanesulfonyl-1',2',3',6'-tetrahydro-[2,4']bipyridinyl 1-[4-(1'-Methanesulfonyl-1',2',3',6'-tetrahydro-[2,4']bipyridinyl-5-yloxymethyl)-piperidin-1-yl]-2-methyl-propan-2-ol (300 g, 0.58 mol) is dissolved in 3000 mL of dichloromethane and the solution is concentrated to 1 L volume at <35° C. This process is repeated with a volume of 500 mL of dichloromethane and then with a volume of 1000 mL of dichloromethane. After the concentration to 1 L volume at <35° C., the solution is diluted with 1000 mL of dichloromethane. In another flask deoxofluor (173 g, 0.74 mol) is dissolved in 1250 mL of dichloromethane and cooled to −30~−40° C. The solution of 1-[4-(1'-methanesulfonyl-1',2',3',6'-tetrahydro-[2,4']bipyridinyl-5-yloxymethyl)-piperidin-1-yl]-2-methyl-propan-2-ol in dichloromethane is added to this solution while maintaining the mixture at −30~−40° C. The reaction is warmed slowly to 20~30° C. and stirred at this temperature for 16 h. The mixture is cooled to 0~10° C. and saturated solution of sodium bicarbonate is added dropwise to pH=6.0~6.5. The mixture is stirred for 30 min and the layers are separated. The aqueous layer is extracted with 1000 mL of dichloromethane. The combined organic layers are washed with 1000 mL of water and concentrated to ~1 L of mixture at <50° C. 1750 mL of acetonitrile are added and the mixture is concentrated to ~1 L of mixture at <50° C. 500 mL of acetonitrile are added and the mixture is heated at 80~82° C. for 30 min to obtain a clear solution. 1250 mL of water are added dropwise at 80~82° C. and the mixture is cooled slowly to 20~30° C. The resulting suspension is filtered. The cake is slurried with 500 mL of a 1:1 mixture of acetonitrile and water and concentrated. The residue is dried under vacuum to give 210 g of crude solid. The crude is purified by chromatography on silica gel eluting with dichloromethane/methanol: 98/2 to provide 165 g of the title compound in 98% purity. (DMSO-d6, 400 MHz), δ=8.23 (dd, 1H, J=2.8 Hz), 7.49 (d, 1H, J=8.8 Hz), 7.36 (dd, 1H, J=8.8, 2.8 Hz), 6.56 (bs, 1H), 3.89-3.86 (m, 4H), 3.37-3.33 (m, 4H), 2.91 (s, 3H), 2.90-2.88

(m, 2H), 2.65-2.63 (m, 2H), 2.42-2.39 (m, 1H), 2.38-2.36 (m, 1H), 2.08-2.03 (m, 2H), 1.71-1.67 (m, 3H), 1.31 (s, 3H), 1.25 (s, 3H) ppm.

EXAMPLE 7

4-{3-Fluoro-4-[1-(2-fluoro-2-methyl-propyl)-piperidin-4-ylmethoxy]-phenyl}-1-methanesulfonyl-1,2,3,6-tetrahydro-pyridine

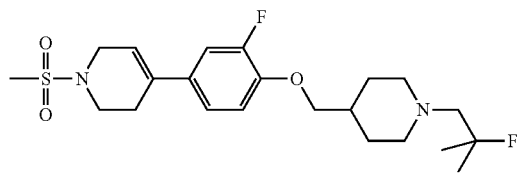

1: 4-(3-Fluoro-4-methoxy-phenyl)-3,6-dihydro-2H-pyridine-1-carboxylic acid tert-butyl ester 4-Bromo-2-fluoroanisole (2.68 g, 12.94 mmol), Preparation 3 (4.40 g, 14.23 mmol) and (1,1'-bis(diphenylphosphino) ferrocene)palladium(II) chloride (528.40 mg, 0.647 mmol) are placed in a resealable tube and purged with nitrogen. Dimethylformamide (40 mL) and a 2 M aqueous solution of sodium carbonate (23.71 mL, 38.82 mmol) are added and the tube is sealed and stirred at 90° C. for 1 h. The reaction is partitioned between ethyl acetate and water. The aqueous layer is extracted with ethyl acetate. The combined organic layers are washed with water and brine, dried over magnesium sulfate, filtered, and concentrated to dryness. The residue is purified by chromatography using a 20 g silica gel cartridge eluting with hexane:ethyl acetate (8:1) to provide 2.6 g of the title compound as a white oil. MS (m/z) 252 (M–55).

2: 4-(3-Fluoro-4-methoxy-phenyl)-1,2,3,6-tetrahydro-pyridine hydrochloride salt Prepared essentially as preparation 6 (step 2) using 4-(3-fluoro-4-methoxy-phenyl)-3,6-dihydro-2H-pyridine-1-carboxylic acid tert-butyl ester as starting material. MS (m/z) 208 (M+1).

3: 4-(3-Fluoro-4-methoxy-phenyl)-1-methanesulfonyl-1,2,3,6-tetrahydro-pyridine 4-(3-Fluoro-4-methoxy-phenyl)-1,2,3,6-tetrahydro-pyridine hydrochloride salt (462.00 mg, 1.90 mmol) is suspended in dichloromethane (10 mL). Triethylamine (479.58 mg, 660.57 μL, 4.74 mmol) and methanesulfonyl chloride (260.59 mg, 176.07 μL, 2.27 mmol) are added and the reaction is capped and stirred at room temperature for 16 h. The reaction is partitioned between dichloromethane and water. The aqueous layer is extracted with dichloromethane. The combined organic layers are washed with brine, dried over magnesium sulfate, filtered, and concentrated to dryness. The crude material is purified by chromatography using a 5 g silica gel cartridge eluting with dichloromethane to provide 349 mg of the title compound as a white solid. MS (m/z) 286 (M+1).

4: 4-(3-Fluoro-4-hydroxy-phenyl)-1-methanesulfonyl-piperidin-4-ol 4-(3-Fluoro-4-methoxy-phenyl)-1-methanesulfonyl-1,2,3,6-tetrahydro-pyridine (1.12 g, 3.93 mmol) is dissolved in dry dichloromethane (20 mL) under nitrogen. The solution is cooled to –78° C. and boron tribromide (11.52 g, 7.85 mL, 7.85 mmol) is added by syringe. The reaction is warmed to room temperature and stirred for 1 h followed by the addition of 5% aqueous sodium bicarbonate and dichloromethane. An insoluble solid is formed and filtered to provide 729 mg of the title compound as a pink solid. $^1$H NMR (CDCl3) δ (ppm): 7.21 (dd, 1H), 7.09 (m, 1H), 6.89 (t, 1H), 3.30 (m, 2H), 3.18 (td, 2H), 2.88 (m, 3H), 2.06 (m, 2H), 1.80 (m, 2H).

5: 2-Fluoro-4-(1-methanesulfonyl-1,2,3,6-tetrahydro-pyridin-4-yl)-phenol 4-(3-Fluoro-4-hydroxy-phenyl)-1-methanesulfonyl-piperidin-4-ol (726.00 mg, 2.51 mmol) is dissolved in 1,4-dioxane (10.36 g, 10.04 mL, 117.57 mmol). p-Toluenesulfonic acid (43.65 mg, 250.93 μmol) is added and the mixture is heated at 60° C. Solid sodium carbonate is added and the reaction is concentrated. The residue is partitioned between water and ethyl acetate, the pH adjusted to 7 with 1 M hydrogen chloride and extracted with ethyl acetate. The organic layer is washed with brine, dried over magnesium sulfate, filtered, and concentrated to dryness to provide 714 mg of the title compound as a white solid. MS (m/z) 272 (M+1).

6: 4-[2-Fluoro-4-(1-methanesulfonyl-1,2,3,6-tetrahydro-pyridin-4-yl)-phenoxymethyl]-piperidine-1-carboxylic acid tert-butyl ester Prepared essentially as Preparation 2 (step 2) using 4-methanesulfonyloxymethyl-piperidine-1-carboxylic acid tert-butyl ester and 2-fluoro-4-(1-methanesulfonyl-1,2,3,6-tetrahydro-pyridin-4-yl)-phenol as starting materials. MS (m/z) 414 (M–55).

7: 4-[3-Fluoro-4-(piperidin-4-ylmethoxy)-phenyl]-1-methanesulfonyl-1,2,3,6-tetrahydro-pyridine hydrochloride salt Prepared essentially as Preparation 6 (step 2) using 4-[2-fluoro-4-(1-methanesulfonyl-1,2,3,6-tetrahydro-pyridin-4-yl)-phenoxymethyl]-piperidine-1-carboxylic acid tert-butyl ester as starting material. MS (m/z) 369 (M+1).

8: 4-{3-Fluoro-4-[1-(2-fluoro-2-methyl-propyl)-piperidin-4-ylmethoxy]-phenyl}-1-methanesulfonyl-1,2,3,6-tetrahydro-pyridine Prepared essentially as Example 2 starting from 4-[3-fluoro-4-(piperidin-4-ylmethoxy)-phenyl]-1-methanesulfonyl-1,2,3,6-tetrahydro-pyridine hydrochloride salt and 2-fluoro-2-methyl-propionic acid. MS (m/z) 443 (M+1).

EXAMPLE 8

4-(4-{1-[1-(2-Fluoro-2-methyl-propyl)-piperidin-4-yl]-ethoxy}-phenyl)-1-methanesulfonyl-1,2,3,6-tetrahydro-pyridine

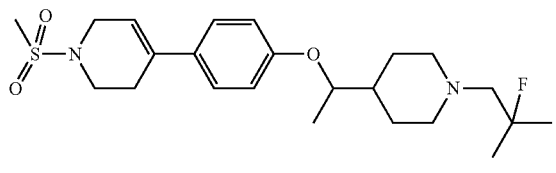

Prepared essentially as Example 2 using Preparation 5 (racemic) as starting material to provide the title compound. The title compound (0.194 g) is separated into its enantiomers using an eluent of 0.2% dimethylethylamine in 100% methanol on a 420×250 mm Chiralpak OJ at 8 mL/min affording 77 mg of isomer 1 (96% ee, RT=10.7 min).

EXAMPLE 9

4-{4-[1-(2,2-Difluoro-propyl)-piperidin-4-ylmethoxy]-phenyl}-1-methanesulfonyl-1,2,3,6-tetrahydro-pyridine

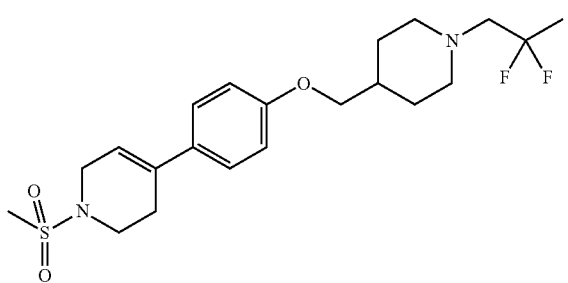

1: Toluene-4-sulfonic acid 2,2-difluoro-propyl ester

To a solution of 2,2-difluoropropanol (0.50 g, 5.20 mmol) in dichloromethane (52.0 mL) and triethylamine (0.50 g, 0.73 mL, 5.20 mmol) at 0° C. is added p-toluenesulfonyl chloride (0.99 g, 5.20 mmol). The mixture is allowed to slowly warm to room temperature over 24 h. The mixture is concentrated and is partitioned between diethyl ether and water. The organic layer is washed with water and brine, dried over magnesium sulfate, filtered, and concentrated to dryness. The material is purified over silica gel to obtain 1.0 g of the title compound as clear crystals. MS (m/z) 250 (M+1).

2: 4-{4-[1-(2,2-Difluoro-propyl)-piperidin-4-ylmethoxy]-phenyl}-1-methanesulfonyl-1,2,3,6-tetrahydro-pyridine To a mixture of Preparation 2 (0.25 g, 0.71 mmol) and toluene-4-sulfonic acid 2,2-difluoro-propyl ester (0.25 g, 0.91 mmol) is added 1,3-dimethyl-2-imidazolidinone (7 mL). The mixture is placed in a Biotage microwave reactor and heated to 175° C. for 1 hour and then 180° C. for 1 hour. The mixture is partitioned between ethyl acetate and water. The organic layer is washed with water and brine, dried over magnesium sulfate, filtered, and concentrated to dryness. The crude material is purified over silica gel to afford 0.03 g of the title compound as a white solid. MS (m/z) 429 (M+1).

EXAMPLE 10

1-Methanesulfonyl-4-{4-[1-(1-trifluoromethyl-cyclopropylmethyl)-piperidin-4-ylmethoxy]-phenyl}-1,2,3,6-tetrahydro-pyridine

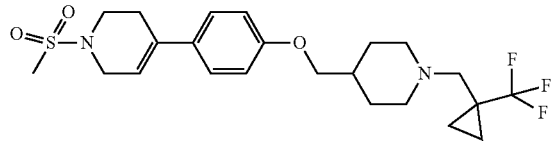

1: 1-(1-Trifluoromethyl-cyclopropanecarbonyl)-piperidine-4-carboxylic acid ethyl ester 1,1'-Carbonyldiimidazole (77.36 g; 467.52 mmol) is added to a solution of 1-(trifluoromethyl)cyclopropanecarboxylic acid (72.04 g; 467.52 mmol) in tetrahydrofuran (600 mL) while keeping the internal temperature below 30° C. Piperidine-4-carboxylic acid ethyl ester (50 g; 311.68 mmol) is added after 10 min and the reaction is stirred under nitrogen atmosphere at room temperature for 16 h. The solvent is removed under controlled vacuum and the residue is partitioned between 2 M aqueous solution of sodium hydroxide (200 mL) and dichloromethane (300 mL). The organic layer is washed with brine (100 mL), dried over magnesium sulphate, filtered and concentrated to obtain 93.45 g of the title compound. MS (m/z) 294 (M+1).

2: [1-(1-Trifluoromethyl-cyclopropylmethyl)-piperidin-4-yl]-methanol 1-(1-Trifluoromethyl-cyclopropanecarbonyl)-piperidine-4-carboxylic acid ethyl ester (50 g; 170.48 mmol) in tetrahydrofuran (350 mL) is added to a solution of 1 M lithium aluminum hydride (170.48 mL; 170.48 mmol) in tetrahydrofuran. The reaction mixture is allowed to warm to room temperature and stirred for 1 h. The reaction mixture is cooled at 0° C. and water/2 M aqueous solution of sodium hydroxide/ water (1:3:1) are added sequentially (8.5 mL:12 mL:8.5 mL). The resulting slurry is filtered over a celite® pad and washed with tetrahydrofuran (200 mL). The organic layer is concentrated under controlled vacuum to afford 17 g of the volatile title compound as colorless oil. The crude material is used without further purification. MS (m/z) 238 (M+1).

3: 1-Methanesulfonyl-4-{4-[1-(1-trifluoromethyl-cyclopropylmethyl)-piperidin-4-ylmethoxy]-phenyl}-1,2,3,6-tetrahydro-pyridine Diisopropyl azodicarboxylate (27.43 g; 128.87 mmol) is added to a solution of triphenylphosphine (33.80 g; 128.87 mmol) in dry tetrahydrofuran (330 mL) at 0° C. The reaction is stirred for 20 min. A suspension of [1-(1-trifluoromethyl-cyclopropylmethyl)-piperidin-4-yl]-methanol (24 g; 99.13 mmol), Preparation 1 (25.89 g; 99.13 mmol) in dry tetrahydrofuran (200 mL) is added dropwise. The reaction is stirred at 0° C. for 10 min and it is allowed to warm to room temperature and reacted overnight. The solvent is evaporated and the resulting slurry is diluted with dichloromethane (350 mL) and washed with 2 M aqueous solution of sodium hydroxide (2×30 mL) and brine (2×30 mL), dried over magnesium sulfate, filtered and concentrated. The pink solid is purified over silica gel eluting with hexane/acetone: 100%; 95:5; 90:10; 80:20 and 70:30, to afford 16 g of title compound, around 80% pure. The solid is treated with 2N aqueous hydrogen chloride. A white solid precipitates and is filtered and dried. The solid is dissolved in water (150 mL) and is basified to pH 12 with sodium hydroxide pellets. The resulting solid is filtered, dried and crystallized with methyl t-butyl ether (100 mL) filtered and dried in the oven at 50° C. to obtain 8 g of the title compound. MS (m/z) 473 (M+1).

An alternative method for the preparation of Example 10 is as follows:

1: 1-(1-Trifluoromethyl-cyclopropanecarbonyl)-piperidine-4-carboxylic acid ethyl ester 1-(Trifluoromethyl)cyclopropanecarboxylic acid (400 g, 2.6 mol) is dissolved in 3.2 L of tetrahydrofuran and cooled to 10~20° C. Carbonyldiimidazole (462.4 g, 1.1 eq) is added in portions. The mixture is stirred at 25-30° C. for 20 min. Then piperidine-4-carboxylic acid methyl ester (445.6 g, 1.2 eq) is added dropwise at <30° C. The mixture is stirred at 25-30° C. for 18~20 h. 3.2 L of water are added dropwise at <30° C. and the solution is concentrated to ~1 L of volume to remove most of tetrahydrofuran. The resulting solution is extracted with dichloromethane (2×). The combined organic layers are washed with 3 volumes of 0.5 M hydrochloric acid and concentrated. 500 mL of methyl tert-butyl ether is added and the solution is concentrated. This process is run twice. The organic layer is concentrated to provide 567 g of the title compound in 95% purity.

2: [1-(1-Trifluoromethyl-cyclopropylmethyl)-piperidin-4-yl]-methanol

Lithium aluminum hydride (208 g, 5.0 eq) is suspended in 3.9 L of methyl tert-butyl ether and the suspension is stirred for 10 min. A solution of 1-(1-trifluoromethyl-cyclopropanecarbonyl)-piperidine-4-carboxylic acid ethyl ester (260 g, 0.93 mol) in 1.3 L of methyl tert-butyl ether is added dropwise at <30° C. The mixture is refluxed for 20 h and cooled to 0~10° C. 500 mL of water are added at 0~10° C. and the mixture is stirred for 30 min. The suspension is filtered and the cake is washed with 1.8 L of methyl tert-butyl ether. The filtrate is concentrated to ~3 L of volume at <35° C. under vacuum. The solvent is displaced with tetrahydrofuran (1.0 L×2) and concentrated to provide 212 g of the title compound in 96.8% purity.

3: 1-Methanesulfonyl-4-{4-[1-(1-trifluoromethyl-cyclopropylmethyl)-piperidin-4-ylmethoxy]-phenyl}-1,2,3,6-tetrahydro-pyridine

[1-(1-Trifluoromethyl-cyclopropylmethyl)-piperidin-4-yl]-methanol (371 g, 1.56 mol) is dissolved in 1.85 L of dichloromethane and triethylamine (237.3 g, 2.34 mol) and the mixture is cooled to 0~10° C. Methanesulfonyl chloride (215 g, 1.2 eq) is added dropwise. The reaction is warmed to 20~25° C. and stirred for 1 h. 1.85 L of water are added dropwise. Layers are separated and the aqueous layer is extracted with 1 L of dichloromethane. The combined organic layers are washed with 1.85 L of water, dried over anhydrous sodium sulfate and concentrated to provide 491 g of an oil that is used for the next step in two batches.

Preparation 1 (197.8 g, 0.781 mol) is dissolved in 1.8 L of dimethylformamide and cooled to 0~10° C. A solution of potassium tert-butoxide (87.6 g, 0.781 mol) dissolved in 1.6 L of dimethylformamide is added dropwise to the solution and the mixture is stirred at 20~30° C. for 30 min. A solution of [1-(1-trifluoromethyl-cyclopropylmethyl)-piperidin-4-yl]-methanol (246 g, 0.781 mol) in 0.5 L of dimethylformamide is added dropwise to the solution. The mixture is heated at ~60° C. and stirred for 1.5 h. It is cooled to 30~40° C., and 4.4 L of water are added dropwise. The mixture is stirred at 30° C. for 1 h and filtered. This process is done with the two batches of [1-(1-trifluoromethyl-cyclopropylmethyl)-piperidin-4-yl]-methanol and the resulting cakes are combined for purification. The cake is washed with 800 mL of a 1:1 mixture of dimethylformamide and water. The solid is stirred with 4 L of dichloromethane and filtered. The filtrate is concentrated and purified by chromatography eluting with dichloromethane to obtain 180 g of the title compound in 99% purity. (CDCl3, 400 MHz), δ=7.31 (d, 2H, J=8.8 Hz), 6.88 (d, 2H, J=8.8 Hz), 6.00-5.98 (m, 1H), 3.97 (s, 2H), 3.82 (s, 2H), 3.55-3.52 (m, 2H), 3.04-3.01 (m, 2H), 2.87 (s, 3H), 2.70-2.60 (m, 4H), 2.06-2.03 (m, 2H), 1.85-1.82 (m, 3H), 1.48-1.45 (m, 2H), 1.03-1.01 (m, 2H), 0.74-0.71 (m, 2H) ppm.

EXAMPLE 11

1-(Methylsulfonyl)-4-(4-(1-(1-((1-(trifluoromethyl) cyclopropyl)methyl)piperidin-4-yl)ethoxy)phenyl)-1,2,3,6-tetrahydropyridine

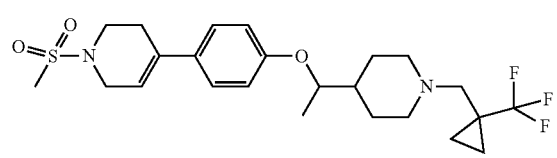

Isomer 2

1. (1-(Trifluoromethyl)cyclopropyl)methanol

To an ice-cold suspension of lithium aluminum hydride (33.91 mmoles; 1.29 g) in diethyl ether (90 mL) is added dropwise over 25 minutes methyl 1-(trifluoromethyl)cyclopropanecarboxylate (16.95 mmoles; 3.00 g) in 30 mL of diethylether. The reaction is stirred at 0° C. for 2 hours. The mixture is quenched by slow addition of 7.5 mL of water, then 15 mL of 5 M sodium hydroxide and 9 mL of water. The thick slurry is vigourously stirred at room temperature for 3 hours. The mixture is transferred to a separatory funnel, diluted with water and extracted with diethylether. The combined organic layers are washed with brine, dried over magnesium sulfate, filtered and concentrated to dryness. 2.37 g of the title compound as a colorless oil are obtained. 2.37 g. $^1$H NMR (CDCl3) d (ppm): 0.762-0.807 (m, 2H), 1.018-1.055 (m, 2H), 3.732 (s, 2H).

2. (1-(Trifluoromethyl)cyclopropyl)methyl methanesulfonate

Prepared essentially as Preparation 2 (step 1) using (1-trifluoromethyl-cyclopropyl)-methanol as starting material. 1H NMR (CDCl3) d (ppm): 0.921-0.975 (m, 2H), 1.182-1.223 (m, 2H), 3.057 (s, 3H), 4.296 (s, 2H).

3. 1-(Methylsulfonyl)-4-(4-(1-(1-((1-(trifluoromethyl)cyclopropyl)methyl)piperidin-4-yl)ethoxy)phenyl)-1,2,3,6-tetrahydropyridine To Preparation 5 (isomer 2) (62 mg, 0.169 mmol), potassium carbonate (70 mg, 0.506 mmol) and acetonitrile (1.12 mL, 21.46 mmol) in a vial is added (1-(trifluoromethyl)cyclopropyl)methyl methanesulfonate (147 mg, 0.675 mmol). The vial is sealed and heated at 110° C. for 16 h. The reaction is diluted with dichloromethane and water. The organic layer is separated and washed with brine, dried over sodium sulfate, filtered, and concentrated in vacuo to afford an off-white solid. The solid is purified by flash chromatography over silica gel to obtain 0.057 g of a white solid. MS (m/z) 487.2 (M+1).

EXAMPLE 12

2-(1-(Methylsulfonyl)-1,2,3,6-tetrahydropyridin-4-yl)-5-((1-((1-(trifluoromethyl)cyclopropyl)methyl)piperidin-4-yl)methoxy)pyridine

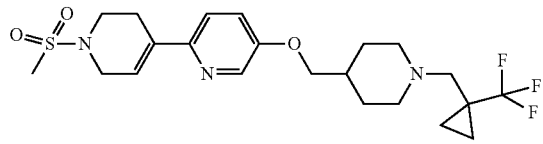

To Preparation 6 (206 mg, 0.586 mmol), potassium carbonate (243 mg, 1.76 mmol) and acetonitrile (2.93 mL, 56 mmol) in a microwave vial is added (1-(trifluoromethyl)cyclopropyl)methyl methanesulfonate (256 mg, 1.17 mmol). The microwave vial is sealed and heated at 140° C. for 2 h then 150° C. for 30 min in the Biotage microwave. The reaction is diluted with dichloromethane and water. The organic layer is separated and washed with brine, dried over sodium sulfate, filtered, and concentrated in vacuo. The residue is triturated with diethylether and the title product is collected via vacuum filtration to obtain 0.181 g of the title compound. MS (m/z) 474 (M+1).

EXAMPLE 13

2-(1-(Methylsulfonyl)-1,2,3,6-tetrahydropyridin-4-yl)-5-((1-(2,2,2-trifluoroethyl)piperidin-4-yl)methoxy)pyridine

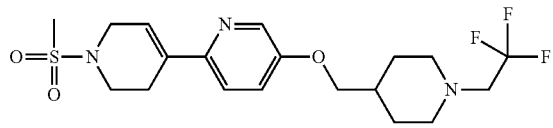

To a solution of Preparation 6 (0.05 g, 0.14 mmol) in acetonitrile (1.50 mL) are added potassium carbonate (0.07 g, 0.56 mmol) and 2,2,2-trifluoroethyl trifluoromethanesulfonate (0.06 g, 0.28 mmol). The reaction mixture is heated at 85° C. for 1 h in a microwave, cooled to room temperature and diluted with water. The mixture is extracted with ethyl acetate and the combined organic extracts are dried over sodium sulfate, filtered, and concentrated. The residue is purified by flash column chromatography over silica gel to obtain 30 mg of the title compound as an off-white solid. MS (m/z) 433 (M+1).

Human GPR119 Activity Assay

A stable cell line expressing human GPR119 off an inducible promoter is generated in 293 T-REx™ cells (Invitrogen). T-REx™ (Tetracycline-Regulated Expression) cell line stably expresses the tetracycline repressor protein and, therefore, allow for inducible expression of the gene of interest (GPR119) with doxycycline. Agonists to the human GPR119 receptor are characterized by measuring increases in the cAMP levels in 293 T-REx™ cells expressing hGPR119. 10,000 cells/well are seeded into a 96-well plate and cultured for 24 h in DMEM supplemented with 10% fetal bovine serum, 15 µg/mL Blasticidin and 200 µg/mL Hygromycin B. Next day, cells are stimulated with 1 ng/mL Doxycycline in DMEM with no further addition of Hygromycin B and Blasticidin. cAMP assay is performed after 18 h incubation with doxycycline. cAMP is determined using the cAMP HiRange HTRF assay (Cisbo International). Cells are washed with PBS and pre-incubated for 15 min with PBS supplemented with 2 mM glucose, 0.25 mM IBMX and 0.1% BSA. Test compounds diluted in the pre-incubation buffer are added and cells are further incubated at room temperature for 1 h. Incubation is stopped by addition of HTRF reagents diluted in the lysis buffer, followed by incubation for 1 h and measurements of fluorescence at 620 and 655 nm. The potency of the agonists is determined as the agonist concentration that gives 50% activation of the hGPR119 mediated cAMP increase (EC50).

All of the exemplified compounds were tested essentially as described above and each were found to have an EC50 value of <10 nM. Example 1 has an EC50 value of 4.61 nM; Example 6 has an EC50 value of 0.95 nM; Example 7 has an EC50 value of 2.13 nM; Example 8 has an EC50 value of 1.10 nM; and Example 10 has an EC50 value of 0.95 nM.

Thus, certain compounds of the present invention are shown to act as agonists of GPR119 in vitro.

Glucagon-Like Peptide 1 Secretion in GLUTag Cells

Effects of GPR119 agonists on glucagon-like peptide 1 (GLP-1) secretion are determined in vitro in GLUTag cells. GLUTag cells are an immortalized murine intestinal enteroendocrine cell line that express the preproglucagon gene and secrete GLP-1 in a regulated manner (Brubaker P L, Schloos J, Drucker D J. Regulation of glucagon-like peptide-1 synthesis and secretion in the GLUTag enteroendocrine cell line. Endocrinology. 1998 139:4108-14). To measure GLP-1 secretion, 15,000 cells/well are seeded in 96-well-plate and incubated for 3 days in DMEM supplemented with 10% FBS and 1% Glutamine. On the day of the experiment, cells are washed twice with the incubation buffer, EBSS supplemented with 5 mM glucose and 0.1% BSA. 150 µL of the incubation buffer containing test compounds is added to each well and cells are incubated at 37° C. for 2 h. After incubation, the supernatant is collected and filtered using 96-well-filter-plates. GLP-1 content in the filtrate is determined with the Mouse/Rat Total GLP-1 Assay (Meso Scale Discovery). The potency of the GPR119 agonists to stimulate GLP-1 secretion is determined as the agonist concentration that gives 50% increase in GLP-1 (EC50).

Examples 6 and 9 were tested essentially as described above and found to have respective EC50 value of 62.7 and 36.8 nM.

Thus, certain compounds of the present invention are shown to have functional activity as agonists of GPR119 in vitro.

Bioavailability

Methods for accessing oral bioavailability are well appreciated in the art. One such reference is *Medicinal Research Reviews* Vol 21 No. 5 382-396 (2001). The oral bioavailability of compounds of the present invention may be estimated essentially as follows.

Cohorts of three 250-400 gram male Sprague-Dawley rats or approximately 10 kg Beagle dogs (female or male) are used. Animals do not need to be fasted for the intravenous (IV) portion of the study. Dogs are IV administered the compounds by cannulated cephalic vein and blood collections are by jugular vein. Animals are first IV dosed at 1 mg/kg and blood samples (0.1 to 0.2 mL) are then collected using EDTA as an anticoagulant at 0.0830, 0.25, 0.50, 1, 2, 4, 8, 12, and 24 h. After at least two days and overnight fasting, the animals are dosed at 3 mg/kg by oral gavage. Blood samples (0.1 to 0.2 mL) are then collected using EDTA as an anticoagulant at 0.25, 0.50, 1, 2, 4, 6, 8, 12, and 24 h. During the course of a study the total of blood (mL) collected is not to exceed 1% of total body weight in grams.

Compound plasma concentrations are measured by LC/MS/MS assays. Data are then analyzed using standard non-compartmental pharmacokinetic analysis. Oral bioavailability is calculated as:

$$(AUC_{0\text{-}inifinity}, \text{oral}/AUC_{0\text{-}inifinity}, \text{IV}) \times (\text{Dose, IV}/\text{Dose, oral}) \times 100\%$$

Example 6 was tested essentially as described above and found to have oral bioavailability of 90% in Beagle dogs. Example 10 was tested essentially as described above and found to have oral bioavailability of 53% in Sprague Dawley rats.

Thus, certain compounds of the present invention have been shown to have good oral bioavailability.

Mouse Gastric Inhibitory Polypeptide (GIP) Assay

Male C57BL/6 mice (8-10 weeks of age, n=20/dose level, n=5/time point) are fasted overnight (16 hr), weighed the following morning, and then orally dosed with vehicle (1% HEC) or various doses of test article at 5 mL/kg. Animals are euthanized by $CO_2$ asphyxiation for 1 minute, and then blood is collected by cardiac puncture at various times (0.5, 1.5, 3, and 6 h post compound dose) into EDTA plasma tubes containing 10 μL/mL DPP4 inhibitor (Millipore, DPP4-010) and $1.1 \times 10^5$ KIU/mL aprotinin. Blood samples are kept on ice until plasma is separated by centrifugation at 3000×g for 5 min. Resulting plasma samples are placed into 96-well plates and stored at −20° C. until analyzed. Measurements of total GIP (measured by Millipore kit EZRMGIP-55K) are performed for each time-point. For each treatment group, the AUC for GIP is determined by applying the trapezoid rule to the timepoint-specific average GIP levels. Potencies were estimated using piecewise linear interpolation across the collection of calculated GIP AUCs above vehicle from a dose response study. Compound potency is defined as the dose and/or concentration of compound that yielded an increase of 350 pg*hr/mL above the vehicle group GIP AUC over the timecourse of the experiment.

Using the procedure essentially as described above, a 10 mg/kg dose of Example 3 resulted in an increase in GIP AUC over vehicle of 762 pg*h/mL; a 10 mg/kg dose of Example 10 resulted in an increase in GIP AUC over vehicle of 762 pg*h/mL; and a 1.6 mg/kg dose of Example 6 resulted in an increase in GIP AUC over vehicle of 422 pg*h/mL.

Certain compounds of the present invention have been shown to stimulate GIP secretion in vivo, which induces insulin secretion, such data indicates potential for use of compounds of the present invention in the treatment of diabetes.

Mouse Oral Glucose Tolerance Test (OGTT)

Normal C57BL/6 mice are fasted overnight, randomized into groups (n=6) and orally dosed with vehicle (1% HEC, 0.25% tween 80, 0.05% antifoam) or 0.9, 2, 6 and 18 mg/kg GPR119 agonist suspended in vehicle. 30 minutes after the compound is administered, mice are dosed orally with a 50% dextrose solution at 3 g/kg. At various times (0, 20, 40, or 60 minutes post glucose), the mice are restrained in cotton gloves or paper towels and 1 mm or less of the tail is cut. A small drop of blood is placed onto Accu-Chek® glucometers (Roche model 22-044217) for glucose measurements. Three glucometers are used to read glucose in each collected sample, with the median value being reported as the final glucose value. Area under the plasma glucose curve (glucose AUC) is calculated for each group and the percentage decrease in the glucose AUC versus the control group is used as a measure of efficacy of the compound to decrease plasma glucose.

Example 6 was tested essentially as described above and found to demonstrate improved glucose tolerance. Example 6 did not influence fasting plasma glucose but significantly decreased postprandial plasma glucose. The data shows that the dose of Example 6 which produces a 50% decrease in glucose area under the curve (ED50) is equal to 0.4 mg/kg.

Thus, a compound of the present invention has been shown to decrease plasma glucose levels in vivo, indicating potential for use of the compounds of the present invention in the treatment of diabetes.

Chronic Treatment of Diet-Induced Obese (DIO) Mice

DIO male C57/BL6 mice are maintained on a calorie-rich diet and have free access to food and water for at least 2 weeks before randomization into groups by weight (n=8) and treatment. Animals are individually housed in a temperature-controlled (24° C.) facility with 12 hour light, 12 hour dark cycle. Body weights range from 34-40 g. Mice are administrated once daily vehicle (1% HEC), 30 mg/kg GPR119 agonist, 30 mg/kg DPPIV inhibitor or a combination of 30 mg/kg GPR119 agonist and 30 mg/kg DPPIV inhibitor. Treatment continues for 3 weeks. Food and body weights are recorded daily before dark photoperiod. Cumulative body weight change is calculated as the daily body weight minus body weight before treatment for each animal and presented as an average for the group. Food intake is measured daily for each animal and combined with the total amount of food consumed by that animal from all previous days to yield cumulative food intake, which is then averaged for the group. At the end of the study OGTT is performed after overnight fasting.

Example 6 was tested essentially as described above where the DPPIV inhibitor is sitagliptin. Sitagliptin alone did not alter body weight or food intake in the study. Example 6 alone produced a mild decrease in both food intake and body weight observed only during the first week of treatment. Combination of sitagliptin and Example 6 produced profound decreases in body weight and food intake that were sustained throughout the course of the study. Example 6 alone or in combination with sitagliptin did not significantly modify plasma glucose levels in this model.

Thus, a compound of the present invention has been shown to decrease food intake and body weight, indicating potential for use of the compounds of the present invention in the treatment of obesity.

We claim:

1. A compound of the formula:

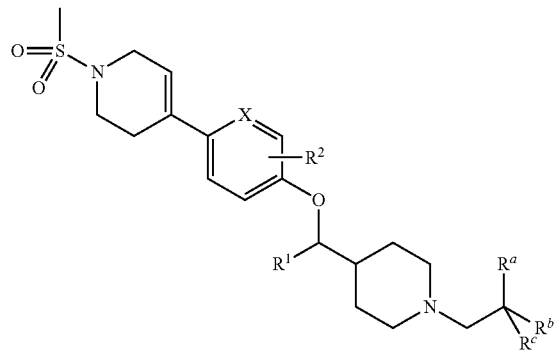

(I)

wherein;
X is selected from N and CH;
$R^a$ is selected from F and $CF_3$;
$R^b$ and $R^c$ are independently selected from F and methyl or combine to form a $C_{3-5}$ cycloalkyl ring;
$R^1$ is selected from H and methyl;
$R^2$ is selected from H and F;
or a pharmaceutically acceptable salt thereof.

2. A compound according to claim 1, or a pharmaceutically acceptable salt thereof, wherein $R^b$ and $R^c$ are independently selected from F and methyl or combine to form $C_3$ cycloalkyl.

3. A compound according to claim 1, or a pharmaceutically acceptable salt thereof, wherein $R^b$ and $R^c$ are methyl or combine to form $C_3$ cycloalkyl.

4. A compound according to claim 1, or a pharmaceutically acceptable salt thereof, wherein $R^a$ is $CF_3$.

5. A compound according to claim 3, or a pharmaceutically acceptable salt thereof, wherein $R^a$ is $CF_3$.

6. A compound according to claim 1, or a pharmaceutically acceptable salt thereof, wherein $R^2$ is H.

7. A compound according to claim 1, or a pharmaceutically acceptable salt thereof, selected from 5-[1-(2-Fluoro-2-methyl-propyl)-piperidin-4-ylmethoxy]-1'-methanesulfonyl-1',2',3',6'-tetrahydro-[2,4']bipyridinyl; and 1-Methanesulfonyl-4-{4-[1-(1-trifluoromethyl-cyclopropylmethyl)-piperidin-4-ylmethoxy]-phenyl}-1,2,3,6-tetrahydro-pyridine.

8. A pharmaceutical composition comprising a compound of claim 7, or a pharmaceutically acceptable salt thereof, and a pharmaceutically acceptable diluent or carrier.

9. A pharmaceutical composition according to claim 8 additionally comprising one or more other therapeutic ingredients.

10. A pharmaceutical composition comprising a compound of claim 1, or a pharmaceutically acceptable salt thereof, and a pharmaceutically acceptable diluent or carrier.

11. A pharmaceutical composition according to claim 10 additionally comprising one or more other therapeutic ingredients.

12. A pharmaceutical composition according to claim 11 wherein sitagliptin is an additional therapeutic ingredient.

13. A method for the treatment of diabetes or obesity, which comprises administering an effective amount of a compound of claim 1, or a pharmaceutically acceptable salt thereof, to a human being or animal in need thereof.

14. A method according to claim 13 for the treatment of type II diabetes.

15. A method for the treatment of diabetes or obesity, which comprises administering an effective amount of a compound of claim 7, or a pharmaceutically acceptable salt thereof, to a human being or animal in need thereof.

16. A method according to claim 15 for the treatment of type II diabetes.

* * * * *